United States Patent [19]

Bontemps

[11] Patent Number: 5,127,395
[45] Date of Patent: Jul. 7, 1992

[54] CRYOGENIC DEVICE FOR SKIN MASSAGE

[76] Inventor: Raymond Bontemps, 5 venue de la Grande Armée, Paris 75116, France

[21] Appl. No.: 614,495

[22] Filed: Nov. 16, 1990

[30] Foreign Application Priority Data

Dec. 19, 1989 [FR] France ................. 89 16776

[51] Int. Cl.⁵ .................. A61H 15/02; A61F 7/00
[52] U.S. Cl. ..................... 128/24.3; 128/403
[58] Field of Search ............. 128/403, 24.1, 401, 128/24.2, 24.3; 165/10; 206/568

[56] References Cited

U.S. PATENT DOCUMENTS

| | | | |
|---|---|---|---|
| 622,350 | 4/1899 | Hans | 128/24.3 |
| 1,177,388 | 3/1916 | Crane | 128/24.1 |
| 1,947,042 | 2/1934 | Glennan | 128/24.3 |
| 2,073,800 | 3/1937 | King | 128/401 |
| 2,929,374 | 3/1960 | O'Gara | 128/24.1 |
| 4,393,918 | 7/1983 | Patry | 165/10 |
| 4,696,302 | 9/1987 | Clark et al. | 128/401 |
| 4,745,909 | 5/1988 | Pelton et al. | 128/24.1 |
| 4,884,560 | 12/1989 | Kuracina | 128/24.1 |
| 4,886,168 | 12/1989 | Bontemps | 206/568 |
| 4,920,956 | 5/1990 | Yamauchi | 128/24.1 |

FOREIGN PATENT DOCUMENTS 472778  3/1929  Fed. Rep. of Germany ..... 128/24.1

Primary Examiner—William H. Grieb
Assistant Examiner—Mark S. Graham
Attorney, Agent, or Firm—Kramer, Brufsky & Cifelli

[57] ABSTRACT

The present invention comprises an assembly including a hollow polyolefin sphere (1) containing a eutectic cooling mixture which is maintained at a temperature of about −20° C. The filled sphere functions to accumulate negative kilocalories and is manipulated by means of an isothermal plastic handle or sleeve in order to apply the sphere to the epidermis. The application of the cold sphere to the epidermis produces vasoconstrictive and vasodilative effects which are beneficial to the maintenance of the epidermal tissues of the skin being massaged. The cryogenic massage can be completed with the application of nutritive substances for the epidermis. The invention can also be used to relieve local aches.

5 Claims, 2 Drawing Sheets

CRYOGENIC DEVICE FOR SKIN MASSAGE

FIELD OF THE INVENTION

The present invention provides a hollow polyolefin sphere containing an eutectic cooling mixture. The polyolefin sphere is equipped with an attached sleeve or handle, which permits use of the sphere for skin massage designed to obtain a vasoconstricting effect on the epidermis. The invention can also be used for relieving local aches.

BACKGROUND OF THE INVENTION

The technique of cryotherapy involves the creation of a vasoconstricting effect on the epidermis, which, through the effect of extreme low temperature, releases the fatty particles contained in the pores. The epidermis, thus massaged, undergoes a second vasodilator effect favorable to the absorption of nutritive substances for the epidermis. Cryotherapy is also used as a means of local anesthesia without secondary effects.

Up until the present time, the cryotherapeutic process involved slowly massaging the epidermal surface with a glass or metal sphere containing an alcohol- or glycerin-based liquid.

The use of a metal sphere leads to a burning phenomenon and thus is prejudicial to treatment.

The glass spheres used in the prior art were maintained in a freezer at −20° C., and the cooling mixture was made up of a low-capacity cooling medium, having a duration of use limited to one hour. These glass spheres, which have a volume of 50 mm, are formed of an open, tapered portion permitting filling with the cooling mixture and a spherical component. The spherical component is used for massaging the skin. This design, which has not proven to be very practical, has numerous disadvantages, which include:
fragility of the device because of the glass structure;
handling difficulties, accentuated by the presence of a filling tube;
limited time the device retains its low temperature.

Accordingly, it is an object of the present invention to provide a device which overcomes the shortcomings of the prior art cryotherapeutic massage devices.

It is another object of the present invention to provide a device comprising a plastic sphere containing a eutectic composition formed from mineral salts which, when kept at a freezing temperature, is solidified by absorbing negative kilocalories.

SUMMARY OF THE INVENTION

These as well as other objects and advantages are obtained in accordance with the present invention which comprises an assembly including a hollow polyolefin sphere (1) containing a eutectic cooling mixture which is maintained at a temperature of −20° C. The filled sphere functions to accumulate negative kilocalories and is manipulated by means of an isothermal plastic handle or sleeve in order to apply the sphere to the epidermis. The application of the cold sphere to the epidermis produces vasoconstrictive and vasodilative effects which are beneficial to the maintenance of the epidermal tissues of the skin being massaged. The cryogenic massage can be completed with the application of nutritive substances for the epidermis. The invention can also be used to relieve local aches

BRIEF DESCRIPTION OF THE DRAWING

The present invention will be better understood by means of the attached drawings, which are given only as examples, and are not limiting.

DETAILED DESCRIPTION OF THE INVENTION

In accordance with the present invention, there is provided a refrigerated sphere (1) made up of a covering of thin polyolefin. The sphere (1) is hollow and contains an equimolecular mixture of alkaline and alkaline earth salts, such as magnesium chloride, magnesium perchlorate and sodium chloride, (2), which constitutes a eutectic composition. Slightly hydrated, the eutectic composition is brought in its entirety to a temperature approaching −25° C. The sphere is filled with the eutectic composition by means of an opening (3) containing an adhered and threaded plug (9). In one embodiment, an isothermal handle (4) is attached to the threaded plug by means of a set screw. The attachment of the handle (4) to the sphere (1) is carried out at the time of use, which allows handling of the cooled sphere without inducing local manual reheating, thereby giving the massage all of its efficacy.

Figure 1:
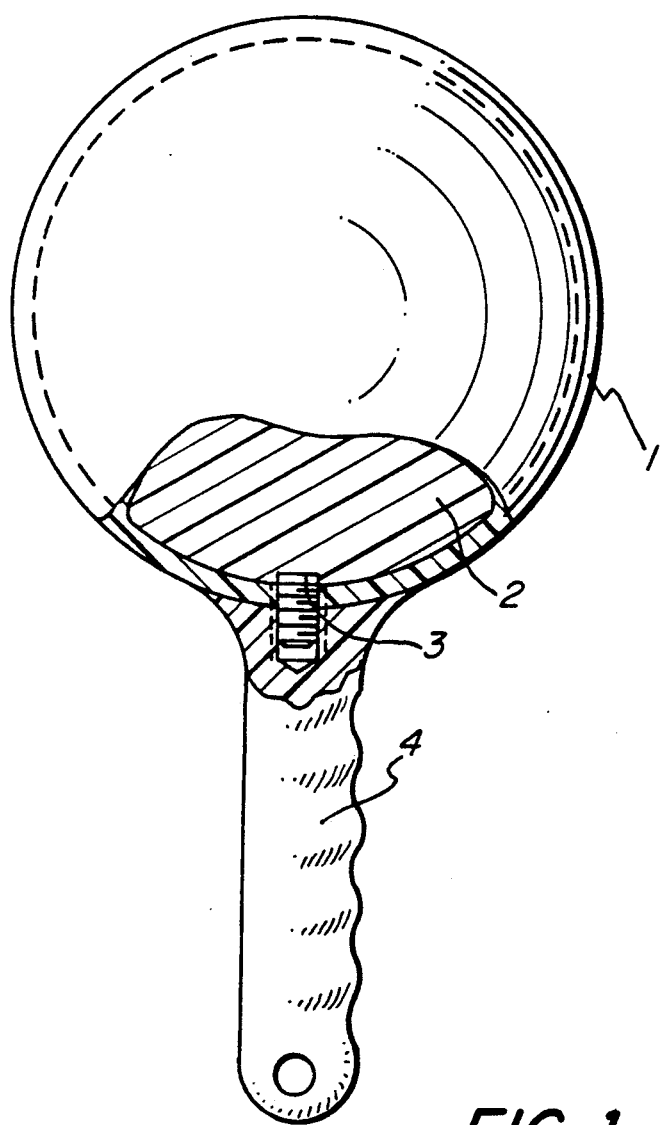
FIG. 1 is an elevational view of a cryogenic device of the present invention with sections removed to show interior elements.
Figure 2:
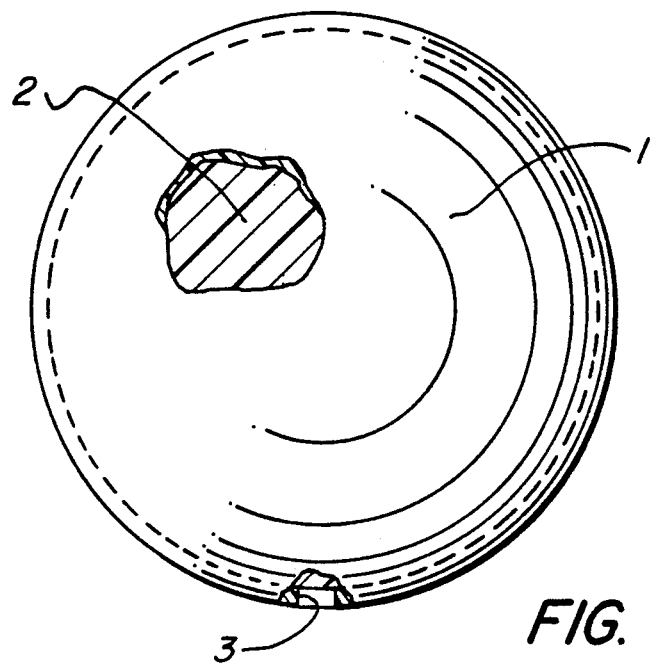
FIG. 2 is an elevation of the sphere with a section removed to show the frozen, cryogenic, eutectic mixture.

FIG. 2 illustrates the sphere used in the device of the present invention which comprises the hollow cooling sphere (1) with a polyolefin covering of several millimeters in thickness. This sphere, whose interior is polished, contains a cooling mixture made up of an equimolecular mixture of magnesium chloride, magnesium perchlorate, and sodium chloride forming a eutectic which is brought in its entirety to a temperature close to −25° C. in a freezer. During use, the cooled sphere is reheated slowing at the melting rate of the eutectic composition, releasing negative kilocalories at the melting rate of the eutectic. The preservation of this cooled sphere surpasses all other similar systems containing only a mixture of alcohol and glycerin maintained liquid at these freezing temperatures.

Figure 3:
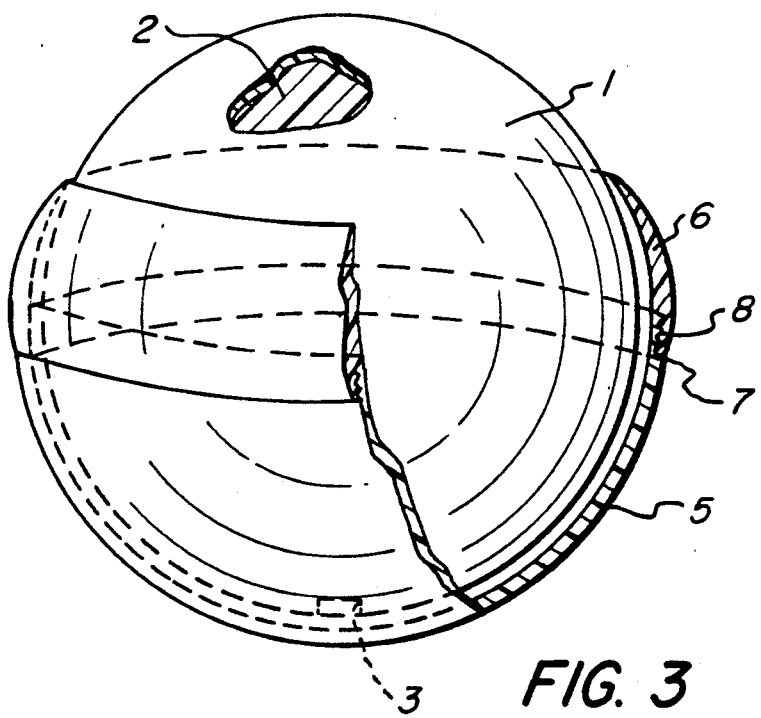
FIG. 3 is an elevation illustrating an alternative embodiment of the invention, wherein the sphere containing the cryogenic eutectic mixture is partially enclosed within an isothermal sleeve.

In FIG. 3, there is illustrated another embodiment of the present invention. In accordance with this embodiment, the sphere (1) is made up of a hollow sphere containing an equimolecular mixture of magnesium chloride, magnesium perchlorate, and sodium chloride, homogenized by crushing and containing several water molecules. The sphere assembly (1) is housed in a plastic sleeve (5) and immobilized in the sleeve (5) by means of a threaded, plastic isothermal ring (6) which is secured to the shell via a threaded portion (10) at level (7). The thus-immobilized sphere cannot escape from its covering because the exterior diameter of ring (6) is less than the maximum diameter of the sphere (1). Shell (5) can freely pivot in its lodging assuring a total utilization of the cooling surface of sphere (1).

The sphere cooled to −25° C. returns the negative kilocalories at the moment of massage by rolling over the skin. The assembly is maneuvered by hand by means of isothermal shell (5).

What is claimed is:

1. A cryogenic device, comprising:
    a hollow sphere for low temperature skin massage formed of polyolefin containing a eutectic composition that solidifies at about −25° C.
    an isothermal sleeve that partially envelops said sphere; and
    a ring having a diameter less than the maximum diameter of said sphere for securing said sphere in said sleeve, wherein said sphere can freely pivot within said sleeve, thereby allowing total utilization of a cooling surface of said sphere.

2. A cryogenic device according to claim 1, wherein said eutectic composition that solidifies at about −25° C. comprises an equimolar mixture of alkaline and alkaline-earth salts.

3. A cryogenic device according to claim 1, wherein said ring is formed of an isothermal plastic and is secured to said sleeve enclosing said sphere via threading.

4. A cryogenic device according to claim 2, wherein said sphere contains an equimolar mixture of magnesium chloride, magnesium perchlorate and sodium chloride containing traces of water forming the eutectic composition which solidifies at −25° C.

5. A cryogenic device according to claim 1, wherein the eutectic composition is enclosed by a thin plastic sphere of polyolefin polished on the exterior of said sphere and rendered airtight.

* * * * *